(12) United States Patent
Irarrázaval et al.

(10) Patent No.: US 11,918,085 B2
(45) Date of Patent: Mar. 5, 2024

(54) METHOD FOR DESIGN OF INSOLES

(71) Applicant: DIGITAL FOOT SPA, Santiago (CL)

(72) Inventors: José Martín Irarrázaval, Santiago (CL); Santiago José Brunet, Santiago (CL); Juan Antonio Irarrázaval, Santiago (CL)

(73) Assignee: DIGITAL FOOT SPA, Santiago (CL)

( * ) Notice: Subject to any disclaimer, the term of this patent is extended or adjusted under 35 U.S.C. 154(b) by 511 days.

(21) Appl. No.: 17/267,786

(22) PCT Filed: Aug. 30, 2018

(86) PCT No.: PCT/IB2018/056656
§ 371 (c)(1),
(2) Date: Feb. 10, 2021

(87) PCT Pub. No.: WO2020/044083
PCT Pub. Date: Mar. 5, 2020

(65) Prior Publication Data
US 2021/0161253 A1 Jun. 3, 2021

(51) Int. Cl.
*A43D 1/02* (2006.01)
*A43B 7/1405* (2022.01)
*A61B 5/103* (2006.01)
*A61B 5/107* (2006.01)
(Continued)

(52) U.S. Cl.
CPC .............. *A43D 1/025* (2013.01); *A43B 7/141* (2013.01); *A61B 5/1038* (2013.01); *A61B 5/1074* (2013.01); *A61B 5/112* (2013.01); *G06F 30/27* (2020.01); *A43D 2200/60* (2013.01)

(58) Field of Classification Search
CPC ...... A43D 1/025; A43D 2200/60; A43D 1/02; A43B 7/141; A43B 17/14; A61B 5/1038; A61B 5/1074; A61B 5/112; A61B 5/0077; A61B 5/6807; A61B 5/7264; A61B 5/7425; G06F 30/27; G06F 30/20; B29C 64/386; B33Y 50/00; G05B 19/4099
See application file for complete search history.

(56) References Cited

U.S. PATENT DOCUMENTS

| 7,206,718 B2 * | 4/2007 | Cavanagh ............ A61B 5/6829 702/155 |
| 7,409,256 B2 | 8/2008 | Lin et al. |
| 7,493,230 B2 | 2/2009 | Schwartz et al. |

(Continued)

FOREIGN PATENT DOCUMENTS

JP 2001321359 A 11/2001

OTHER PUBLICATIONS

Owings, T. et al. "Custom Therapeutic Insoles Based on Both Foot Shape and Plantar Pressure Measurement Provide Enhanced Pressure Relief". Diabetes Care May 2008; 31(5): 839-844; https://doi.org/10.2337/dc07-2288.

*Primary Examiner* — Ziaul Karim
(74) *Attorney, Agent, or Firm* — CALDERON SAFRAN & COLE P.C.; Corinne Marie Pouliquen

(57) ABSTRACT

The invention provides an algorithm-driven method that uses a set of mathematical techniques and numerical procedures to carry out an automatic design for therapeutic insoles. Objectives of the invention include relieving soft tissue overpressure, aligning bone segments and redistributing loads located in specific zones of the foot.

13 Claims, 11 Drawing Sheets

(51) Int. Cl.
*A61B 5/11* (2006.01)
*G06F 30/27* (2020.01)

(56) References Cited

U.S. PATENT DOCUMENTS

| | | | |
|---|---|---|---|
| 9,460,557 B1* | 10/2016 | Tran | G06T 15/205 |
| 9,910,425 B2 | 3/2018 | Spector | |
| 2004/0133431 A1* | 7/2004 | Udiljak | A43B 17/00 |
| | | | 705/26.1 |
| 2009/0287191 A1* | 11/2009 | Ferren | A61B 5/6848 |
| | | | 600/504 |
| 2014/0277658 A1* | 9/2014 | Hanft | G05B 15/02 |
| | | | 700/97 |
| 2016/0249829 A1* | 9/2016 | Trabia | A61B 5/1128 |
| | | | 600/592 |
| 2017/0068774 A1* | 3/2017 | Cluckers | A61B 5/112 |
| 2018/0140053 A1* | 5/2018 | Van Heijkamp | G05B 19/4099 |

* cited by examiner

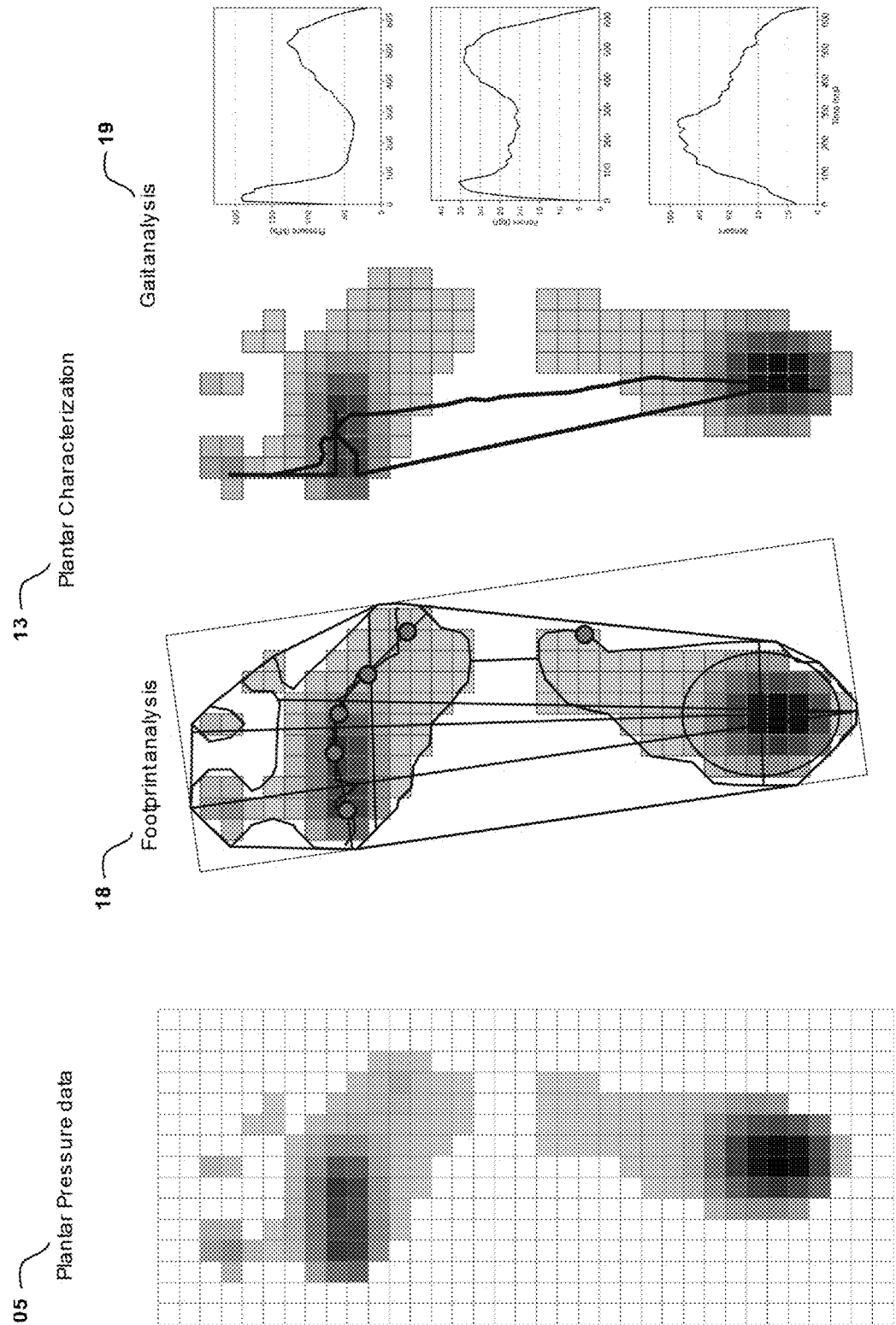

METHOD FOR DESIGN OF INSOLES

CROSS-REFERENCE TO RELATED APPLICATIONS AND CLAIM TO PRIORITY

This application is a national stage application of International Application No. PCT/IB2018/056656 filed Aug. 30, 2018, the disclosure of which is incorporated herein by reference and to which priority is claimed.

FIELD OF THE INVENTION

An automated method for the design of therapeutic insoles.

2. BACKGROUND OF THE INVENTION

The main objectives of a therapeutic insole are the relief of peak pressures under the foot and the bone alignment of the lower limb, which can produce pain and discomfort during the gait or standing of an individual.

During the past, insoles have been made through manual processes and/or design methods based on the common sense, which is not always supported by scientific principles. The insole personification, their shape and the material selection depend on the orthopedist experience, who normally have low or null degree of training, and a high lack of theorical and quantitative support. In addition, medical prescriptions made to a patient by a traumatology professional may only include minimum or too generalized indications, which have no important relevancy in the insole final design.

Although significant technology advances have taken place in manufacturing processes, which consider the use of CNC systems or 3D printing, the current design process of insoles still uses techniques based in foot molds, which are manually or digitally modified later, according to the particular orthopedist criteria.

Independently of the used fabrication system, therapeutic insoles will maintain a high degree of imprecision and limited effectiveness while not using an automated design method, which integrate all the variables that may influence in their conception, considering well-defined and robust criteria. Besides, the manual process inherent to the past methods will be related to higher costs, due to the higher labor intensity.

The present invention provides an algorithm-driven design method for the design of therapeutic insoles, which is capable of implement a plurality of variables from different origin, in a common mathematical language, for the analysis of the individual behavior and the generation of a personalized therapeutic insole.

There are publications that have tried to solve these problems, and have presented methods or systems for the automatization in the insole fabrication and the use of scanner pressure plates and other advanced devices to take patient's samples. However, they have been insufficient to achieve a real and efficient solution, which implies an optimal insole design with no manual processes. As example, some of these publications are described below:

JP 2001/321,359 is a publication that details the importance of the alignment of bone based on sole pressure distribution. However, it discloses to generate a mapping of the plantar pressure, based exclusively on said parameters (alignment of bones). This provides for the manufacturing of an insole that allows the reduction of pressures in the plant, such that the distribution is averaged.

U.S. Pat. No. 7,206,718 describes a method for designing and producing a sole, which reduces the pressures on a person's plant. It mentions the problems of other prior art, related to the fact that they are usually made based on a negative shape of the foot. It describes the measuring of the 3D shape of the foot (col. 2), the distribution of plantar pressures (col. 2), as well as medical information ("practitioner input", col. 5). It also describes aligning the sole of the foot, with respect to the shape of the foot (col. 6). Subsequently, a base sole is chosen, which best corresponds to the 3D shape of the foot, and then, from the pressures and alignment, regions where said predetermined sole is to be modified are identified, such that the pressures on the sole be minimized (col. 10, claim 1). The impact of a practitioner on the design, though barely mentioned, is not detailed. The use of an automatic learning system is also not mentioned.

"Custom Therapeutic Insoles Based on Both Foot Shape and Plantar Pressure Measurement Provide Enhanced Pressure Relief", DIABETES CARE, VOLUME 31, NUMBER 5, MAY 2008, is an essay, wherein data, such as medical history (but it is not specified that it was actually used), plantar pressures, and rubber impressions (3D shape) are transmitted to different companies, for them same to make orthopedic soles. In particular, it is taught that company Z used an algorithm that took into account the pressure profile, and the 3D shape, to generate a 3D model of a sole, which was later considered adequate. Among the companies evaluated (X, Y, Z), it was determined that company Z performed the better. However, it is not specified to obtain reference values starting from the medical history, nor the alignment, or the use, of an automatic learning system is mentioned.

On the other hand, U.S. Pat. Nos. 7,409,256, 7,493,230 and US 2016/249,829 extensively detail the acquisition of plantar pressure profiles, although only U.S. Pat. No. 7,493,230 and US 2016/249,829 mention the scanning of the 3D shape. These documents describe creating a sole from said data.

US 2014/277,658 features a system for designing and manufacturing footwear, which considers scanning the 3D shape, and the alignment of a patient's foot ([0010-0013]). It also considers clinical parameters, such as surgical, dermatological, and neurological conditions [0013, 0014]. The pressure analysis, though mentioned, is it not detailed in any extent. On the other hand, the described system is not specific in detailing the processing of the data to produce a design, but simply speaks of "adequate programming", which leaves it in a rather generic scope. Finally, the alignment or the use of an automatic learning system is not mentioned.

Finally, U.S. Pat. No. 9,910,425 describes how to create a sole, starting from the scanning of the 3D shape of the foot, and the alignment of the spine and leg. It does not mention the pressure profile.

It is seen that, in the prior art, various methods are disclosed for designing orthopedic soles, that include scanning the 3D shape and plantar pressure.

However, it does not include specific details of the processing of clinical parameters. Nor is a parameterization observed from a previous analysis of data from scientific information sources (publications).

Thus, a need is identified to accomplish an invention that takes into account this information, for the design of insoles that provide for a more comfortable footwear.

3. SUMMARY OF THE INVENTION

A method for the design of therapeutic insoles is disclosed which comprising the steps of: providing a plurality of medical criteria about the biomechanics of the lower extremity of the body and a plurality of therapeutic insole design criteria, which parameters are previously determined in an arbitrary manner; providing a database with inner shape data information, which includes the shape and characteristics of the main shoe trademarks and models in the market; determining an individual-specific input by an exam and/or clinical interview based on the existence of concomitant pathologies and conditions, indicators of physical activities, posture observation, anatomical dimensions and foot anthropometry providing a first device to measure the dynamic and/or static plantar pressure of the foot; determining, by the first device, a set of plantar pressure data, for the measurement of foot function and gait analysis, during a determined interval of time; providing a second device to measure the alignment of bone segments of the lower extremity of the body; determining, by the second device, a set of image data for the measurement of bone segments alignment of the lower extremity of the body and the relation between them; providing an algorithm-driven design to carry out the design of a plurality of three-dimensional elements, by determining at least the following: a set of implementation instruments, which contain the mathematical and programming implementation of all the recommendations and medical criteria that were compiled in the systematic review and internal studies; an individual characterization, which contain the diseases, pathologies, physical activities, and all the medical-related analysis, based on the individual-specific input obtained previously. a set of plantar characterizations of the individual, which contain a footprint analysis and gait analysis, based on the data obtained by the first device; a set of alignment characterizations of the individual bone-alignment, which contain a representation and inclination analysis, based on the data obtained by the second device; a set of shapes are determined from the inner shape data and the plurality of characterizations, which are weighted individually or correlated; a diversity of geometric parameters from the previously mentioned shapes, which value types may be angles, lengths and percentages; using said algorithm-driven design to determine the plurality of three-dimensional elements.

4. DESCRIPTION OF THE DRAWINGS

FIG. 3 illustrates plantar characterization, which is constructed based on plantar pressure data.

5. DETAILED DESCRIPTION OF THE INVENTION

The present invention provides an algorithm-driven method which use a set of mathematical techniques and numerical procedures, to carry out an automatic design of therapeutic insoles. One of the objectives of this invention is the relief of overpressure in soft tissues, the alignment of bone segments and the redistribution of loads located in specific zones of the foot.

Figure 1:
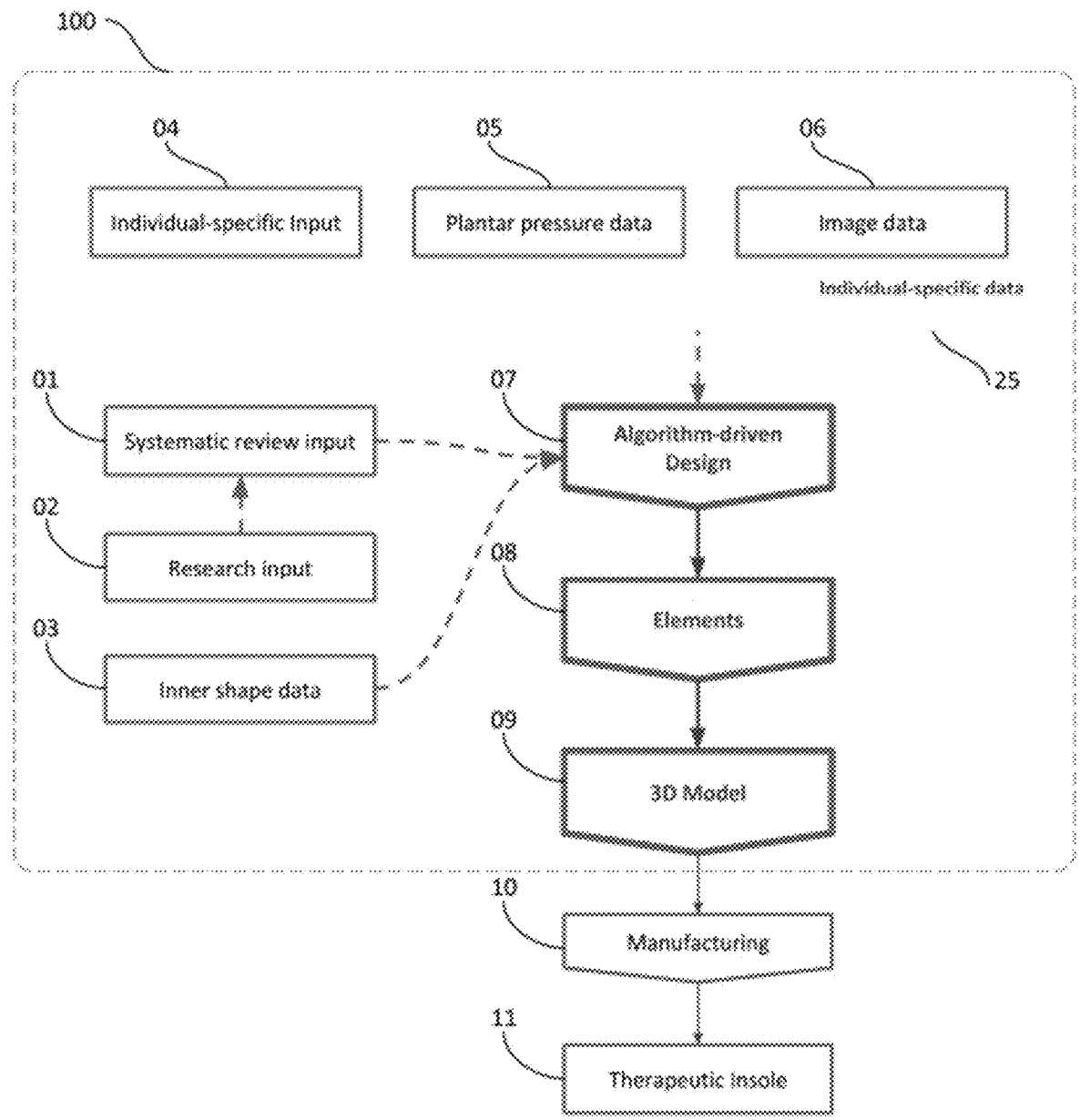
FIG. 1 is a flowchart showing an embodiment for a method for measuring individual data, creating a 3D model and manufacturing a therapeutic insole, which uses an algorithm-driven design.

A method, shown schematically in FIG. 1, substantially comprises a mathematical characterization of the gait anomalies in an individual, and their relation with previously defined medical criteria, for the construction of a three-dimensional model, which is then used for the manufacturing of a unique therapeutic insole for a given individual. This method also provides traceability in each part of the process, for later analysis and eventually improvements in the obtained insoles.

SYSTEMATIC REVIEW INPUT 01. A set of systematic reviews 01 are previously carried out in an independent process, to collect and analyze studies and publications, which contain the state of the art about the therapeutic insole design, and biomechanical relations of the lower extremity of the body and foot. Corresponding algorithms, parse the results founded in the literature, to convert the same into numerical equations and/or operations.

These systematic reviews can comprise a subset of internal studies 02, published or not, carried out by the inventors of this patent, by themselves or with experts in several disciplines like engineering, kinesiology and medicine.

The plurality of systematic reviews 01, together with their analyses, conclusions and numerical implementation in the mentioned algorithms, are stored in a centralized database, which can be updated periodically with the inclusion of new studies carried out.

According to the experience of the inventor the collected medical criteria should at least contain these categories:
  desired insole objectives;
  foot anatomy a;
  measurement instruments;
  normality and anomaly ranges;
  geometry of insole elements;
  interrelation of insole elements;
  others.

Desired insole objectives: should at least comprise the goals that have to be reached to accomplish an optimum insole design. For example, redistribution of plantar foot pressure, alignment of bones segments, comfort feeling, pain reduction, among others.

Foot anatomy: should at least comprise the dimension, areas and important points of the foot, such as the location of protuberances or bones extremities which are useful for the construction of the insole elements. Amongst them are for example the longitudinal axis of the foot, the forefoot, midfoot and rearfoot contours, peak pressure, center of pressure, metatarsal heads location, heel location, fingers location, among others.

Measurement instruments: should at least comprise those tools which are used to find and identify some conditions and geometries of the foot, besides the alignment of the lower limb and their axes. Amongst them are for example some instruments for plantar description like Clarke angle, Chippaux-Smirak index, Arch index and center of pressure excursion index CPEI. Related to biomechanical description of the lower limb are instruments like Helbing line, subtalar joint pronation/supination angle, Navicular drop and Longitudinal Arch angle, among others.

Normality and anomaly ranges: should at least comprise those values which are most common in the population, with the respective segmentation of races and cultures, for each variable used in the design process. Amongst them are, for example, the normal pressure range, as measured in the metatarsal heads location, the variability range of the equilibrium center location, or the normal deviation in the center of pressure during the gait, among others.

Geometry of insole elements: should at least comprise those criteria relevant to shape, dimension and location of the different insole elements 08, which together make up a therapeutic insole, and those geometric parameters 17 which influence them.

Interrelation of insole elements: should at least comprise the establishes description of the coexistence and dependence between the different insole elements 08 that make up a therapeutic insole, and how the specific configuration of one of them can influence the others, and vice versa.

INNER SHAPE DATA 03. A bad fit of the insole in the shoe, where it is fitted into, can strongly distort its performance, and thus the inclusion of the shoe conditions where the insole will be placed is necessary and determinant. For this purpose, it should be taken into account the Inner shape data 03, of the specific shoe in which the therapeutic insole is used. Said Inner shape data 03 includes at least the size, the internal perimeter, the internal shape and the midsole structure of the specific-shoe.

The Inner shape data 03 construction is carried out in an independent process, by generating a complete database, which contains the information of the main shoe trademarks and models in the market, and their specific shapes, with one or more devices for this purpose, or an estimation of the practitioner in other case.

INDIVIDUAL-SPECIFIC DATA 25. The therapeutic insole design considers the unique characteristics of each individual, as a base to provide a particular solution for each foot, in a given context. A plurality of these unique characteristics generates an Individual-specific input 04, a set of Plantar pressure data 05 and a set of Image data 06. It may also include a 3D Scan data 24, such as shown later in embodiment 101.

Not all the relevant inputs for the therapeutic insole design can be obtained through electronic devices, and thus the inclusion of an individual-specific input 04 is an essential stage of the proposed design method. It mainly considers the identification and personal data, anamnesis, concomitant diseases, physical activity indexes, body dimensions and foot anthropometry. In some embodiments, it may also include practitioner and/or physician diagnosis. These inputs are collected using digital means by the practitioner and/or the person which will design the insole.

The proposed design method considers the recollection of Plantar Pressure data 05, given a set of plantar pressure exams, obtained through a plantar pressure device. Such a device may be a Footwork pressure plate by AMCube from UK, which has an array of pressure sensors distributed in a plate. The gait of the individual is measured through at least three dynamic samples of each foot, and the standing of the individual through at least one static sample for 15 seconds. It is possible to carry out the insole design with only one pressure dynamic sample, however, increasing the number of samples, will consequently increase the accuracy of the provided solution.

The proposed design method also considers the alignment of the lower limb of the body, which is obtained through a set of Image data 06 of the lower limb of the individual, obtained with a device for that purpose. Such a device may a Nikon D90 photographic camera. The individual Alignment characterizations 14 are then obtained thought an image-recognition process, like the alignment of the tibia and calcaneus of both feet.

Figure 2:
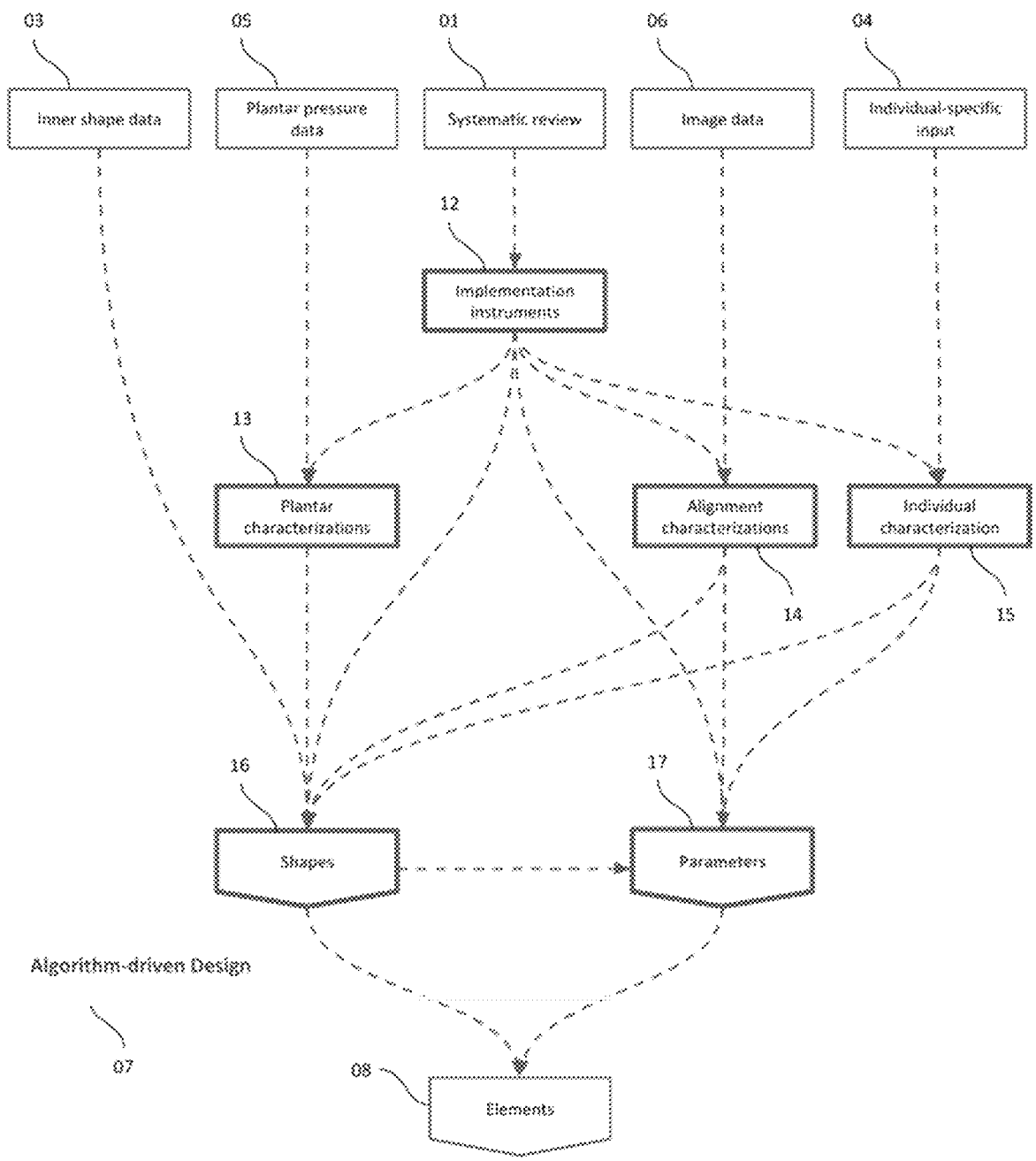
FIG. 2 is a flowchart showing the different parts comprised in said algorithm-driven design method, for interpreting and characterizing specific data from an individual, building shapes and parameters, and constructing elements to build said 3D model.

ALGORITHM-DRIVEN DESIGN 07. The Systematic Review input 01, in conjunction with the Inner shape data 03 and the Individual-specific data 25, provides the needed information to perform an algorithm-driven design 07, which gives as result the Insole elements 08 that make up a 3D Model 09, as shown in FIG. 2. The Individual-specific data 25 was obtained in the previously described processes, contains the Individual-specific input 04, the Plantar Pressure data 05 and the Image data 06.

The algorithm-driven design 07 involves the generation of a set of Implementation Instruments 12, which contain the mathematical and programming implementation of all the recommendations and medical criteria, that were compiled in the Systematic review input 01. This set of instruments are taken as the necessary base to carry out all the characterizations 13, 14 and 15, to construct the Shapes 16, and to calculate the Parameters 17, as explained below.

The algorithm-driven design 07 carries out a group of characterization processes. This group should at least contain:

a Plantar Characterization 13, for each of the samples obtained in the Plantar Pressure data 05;

an Alignment Characterization 14, for the set of images obtained in the Image data 06;

an Individual characterization 15, for the information collected through the Individual-specific input 04.

The algorithm-driven design 07 carries out a construction of Shapes 16 which, in conjunction with the calculated Parameters 17, are used to build the Insole Elements 08, which make up the 3D Model 09 of the therapeutic insole 11.

Plantar characterizations 13. The proposed method considers the building of one Plantar Characterization 13, for each one of the plantar pressure exams, of dynamic and/or static type, of any of the feet, in accordance with the medical criteria, summarized and implemented through the Implementation Instruments 12.

The Plantar characterization 13 calculates a set of three-dimensional geometric shapes, made up of Points, Lines, Polygons and Curves, among others. These are calculated through mathematical calculations and matrix operations.

The Plantar characterization 13 is separated into 2 analyses: these are a Footprint analysis 18 and a Gait analysis 19, as shown in FIG. 3.

A Footprint analysis 18 infers the geometry of a number of zones and quantities along the foot, based on the peak and mean pressure values, as measured in a dynamic pressure examination, through contour levels. Among those values, there are for example a medial axis, a lateral axis, a bisector axis, a heel ellipse, a longitudinal medial arch, a ball of the foot, metatarsal heads location, fingers location, a fifth metatarsal tuberosity, among others.

Further, the Footprint analysis 18 identifies some pathologies and conditions related to pressure data, like pressure concentration on given zones and metatarsal pain.

A Gait analysis 19 infers the gait behavior of the individual, based on sensor values during time, which are measured at a given sampling frequency, that depends on the plantar pressure device used for this purpose. Among the quantities calculated in the Gait analysis, there is, for example, a center of pressure path, a peak pressure path, an individual weight, a set of support areas, a set of impact loads, heel and toe lifts, among others.

Besides, the Gait analysis 19 identifies some pathologies and conditions related to behavior, like flatfoot, cavus foot, high-arched foot, supinator or pronator foot, among others.

The set of obtained results with the Footprint analysis 18 and Gait analysis 19, of all the Plantar pressure data 05 of the individual, are then individually weighted for the construction of the Shapes 16. The larger the number of Plantar characterizations 13 obtained, the more representative and accurate will be the resulting Shapes. Mainly, because the dependency of the samples with the sensor size will decrease, thus making the shapes smoothest. Further, the construction of Shapes, based on different Plantar characterizations 13, provides for the homologation between different devices to measure plantar pressure, different manufacturers and different sensors size, as available to the public.

Alignment characterizations 14. The proposed method considers the building of one Alignment Characterization 14, for each one of the image data of the lower limb of the body, in accordance with the medical criteria summarized and implemented through the Implementation Instruments 12.

The Alignment characterization 14 calculates a set of three-dimensional geometric shapes made of Points, Lines, Polygons and Curves, among others. These are calculated through mathematical calculations and matrix operations, based in image-recognition algorithms.

Figure 4A:
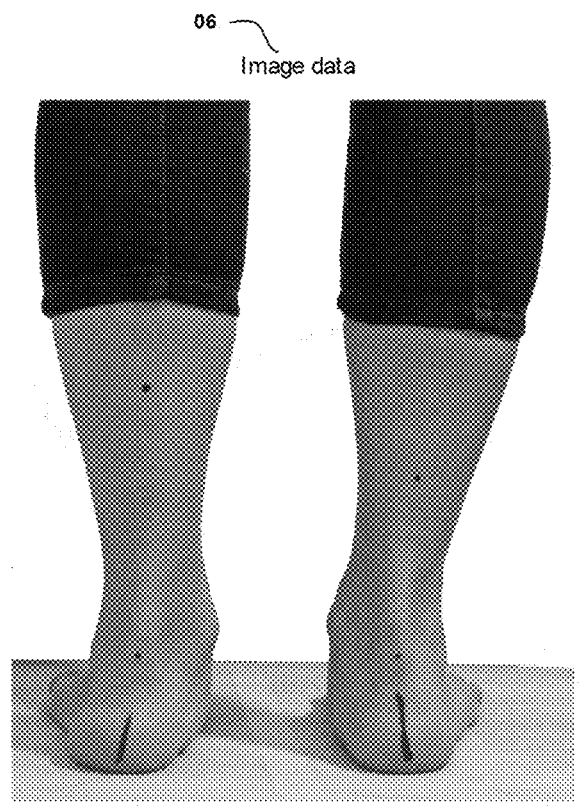
FIG. 4 illustrates alignment characterization, which is constructed based on image recognition data.
Figure 4B:
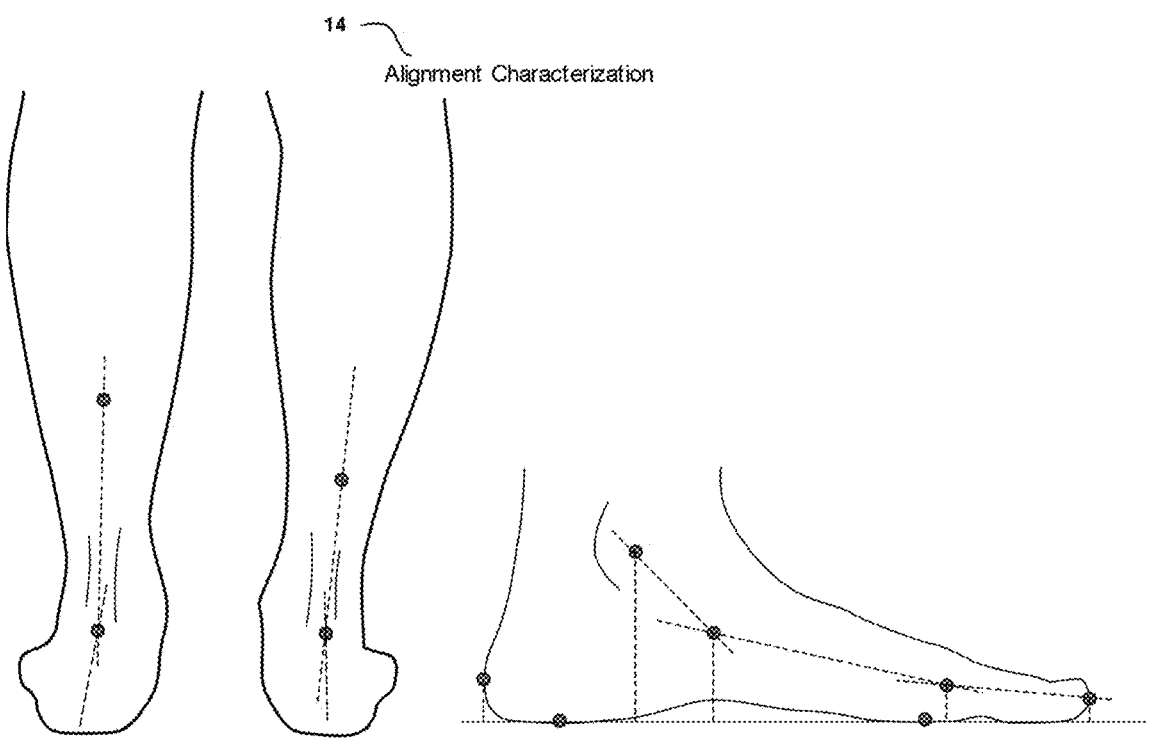

The Alignment characterization 14 includes the position, inclination and orientation of the tibia axis, calcaneal axis, as well as other quantities that may be relevant to obtain the information about the posture and the loads transmission of the body on the feet, as shown in FIG. 4.

Further, the Alignment characterization 14 identifies the bone representation of the foot, and some conditions and pathologies related to the alignment, which are for example the generation of injuries or pronation and supination grade of the ankle.

The set of obtained results with the Alignment Characterization 14, of each the image data 06 of the individual, are then individually weighted for the construction of the Shapes 16 and the calculation of the Parameters 17.

Individual characterization 15. The proposed method considers the building of an Individual characterization 15, with the set of data collected through the Individual-specific input 04, in accordance with the medical criteria summarized and implemented through the Implementation Instruments 12.

The Individual characterization 15 reads and interprets the medical history and anamnesis, concomitant diseases, physical activity indexes, body dimensions and foot anthropometry, among others, and all the relevant data required to carry out the therapeutic insole design.

The set of obtained results with the Individual characterization 15 are used for the construction of the Shapes 16.

Shapes 16 and Parameters 17. The Elements 08 which make up a 3D Model 09 of the Therapeutic Insole 11 are built based in a set of Shapes 16 and Parameters 17, as determined previously, in accordance with the medical criteria summarized and implemented through the Implementation Instruments 12.

Figure 5:
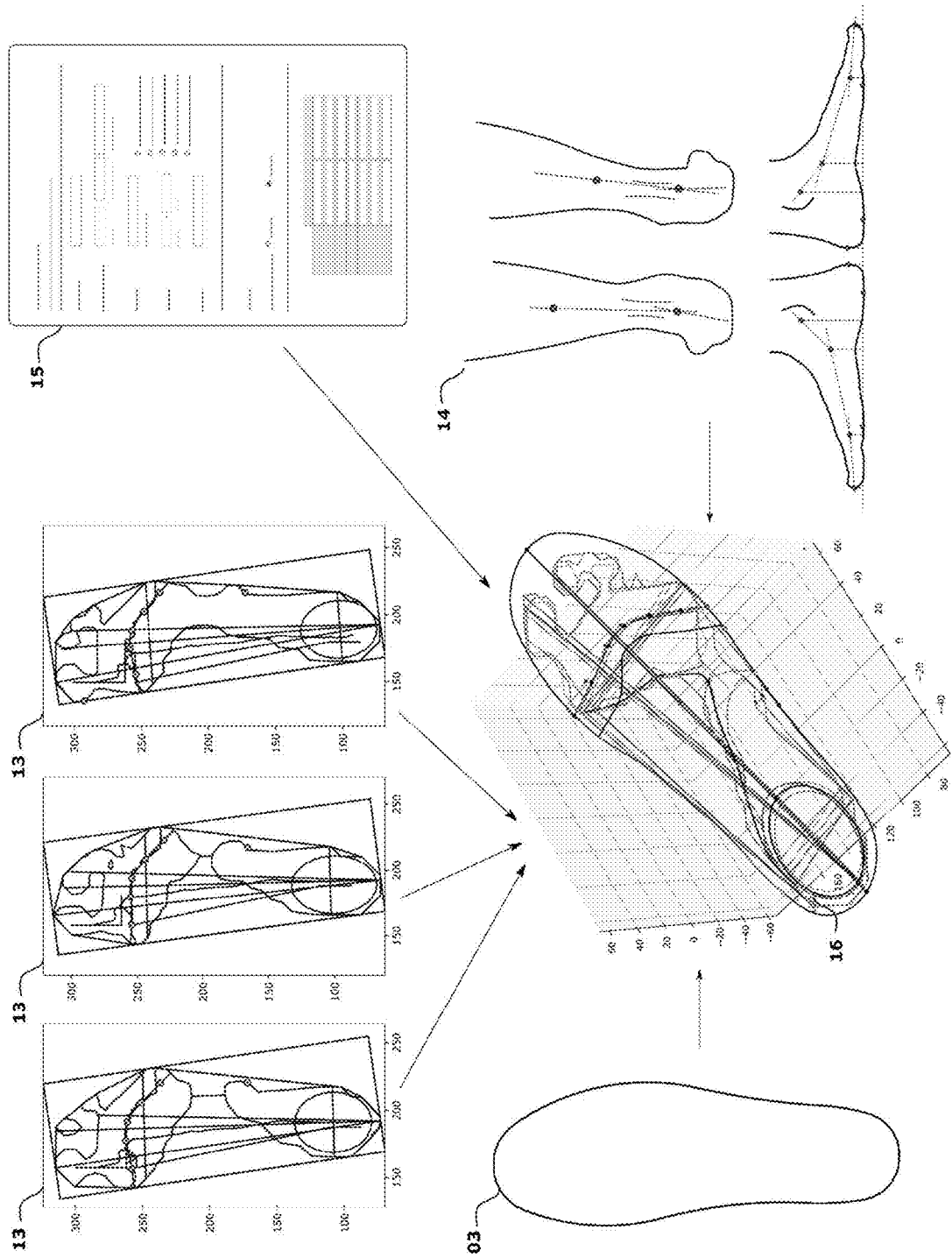
FIG. 5 illustrates the process for the creation of the shapes, which are constructed with a set of plantar characterization, an individual characterization, alignment characterization and inner shape data.

As shown in FIG. 5, a set of Shapes 16 are calculated from the Inner shape data 03, a plurality of characterizations, that include the Plantar characterization 13, the Alignment characterization 14, the Individual characterization 15, and any other characterization needed, which are weighted in an individual or correlated way with the Systematic review input 01, through the Implementation Instruments 12.

The Parameters 17 contain geometric information and have the values that will be used to actually build the three-dimensionality of the Shapes 16. Among others, value types may be: angles, lengths and percentages, and they have direct influence in the dimension and location of those Elements 08.

It is schematically shown in FIG. 6A to FIG. 6E how the parameters are used in the construction of the Longitudinal Arch, which is an example of the Insole Elements 08, implemented in the design method.

Figure 6A:
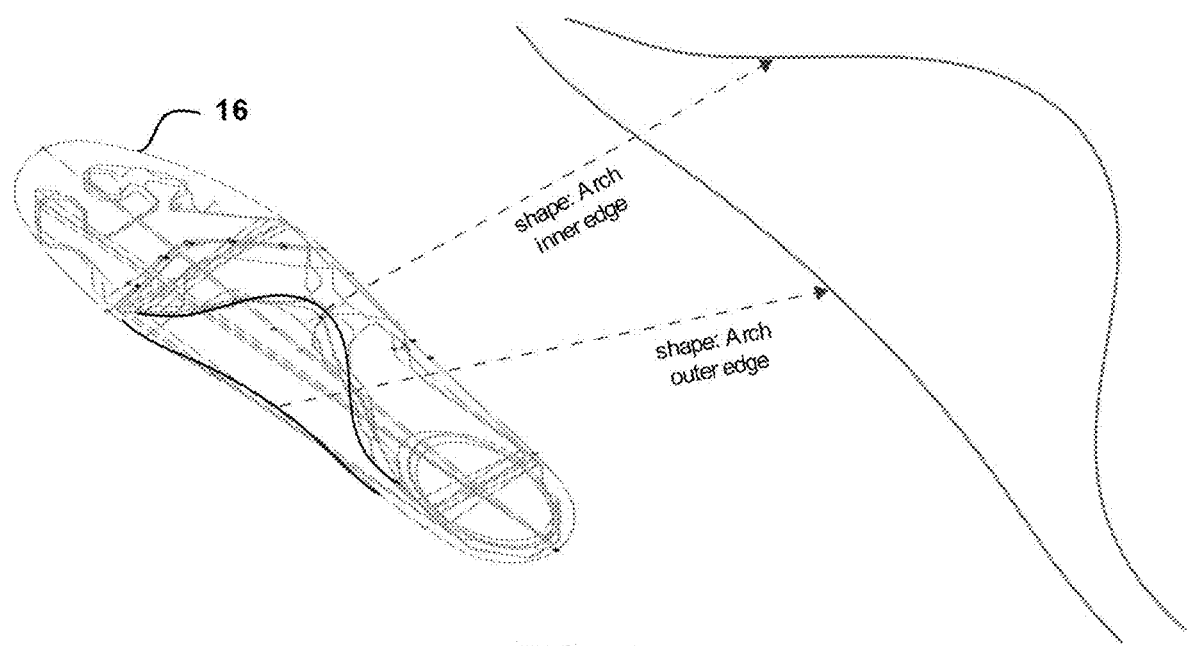
FIG. 6 illustrates the construction of the Arch Element, given a set of Shapes and a set of Parameters.

In a first step, curves or quantities for the construction of a certain insole element 08, but only those that are considered from the generated group of Shapes 16, as shown in FIG. 6A. In this particular case, only two curves are taken into account to build the Arch, and these are the Arch inner edge (or medial edge), and the Arch outer edge (or lateral edge).

Figure 6B:
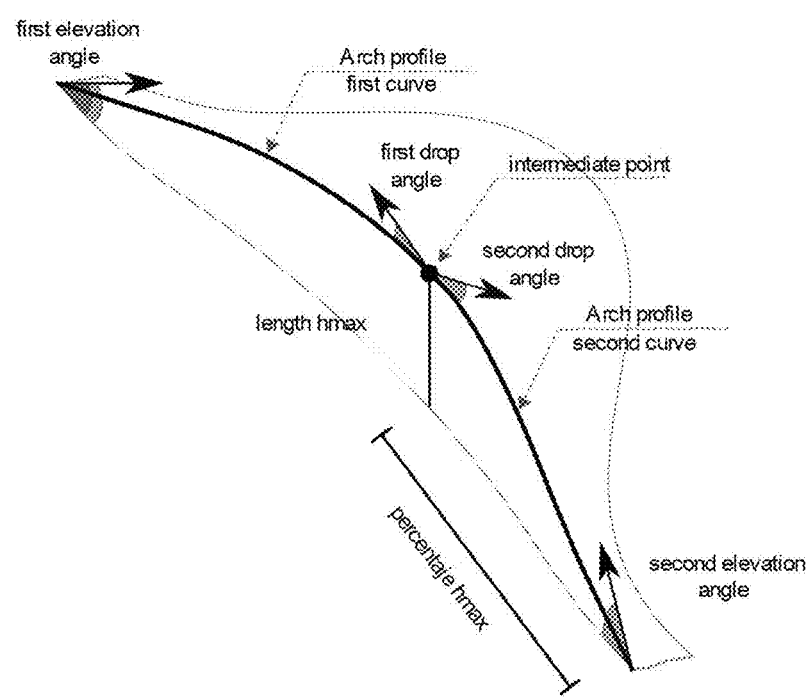

In a second step, the construction of the Arch profile takes place. The Arch profile is formed by two curves, as shown in FIG. 6B, indicated here as Arch profile first curve and Arch profile second curve. The curves are built parametrically with control points, following some of the mathematical description methods frequently used in computer graphics, as for example Polynomial curves, Spline curves, Bezier curves or Nurbs curves, among others. Based in the maximum height of the arch and the location of that height, both values given as parameters (here indicated as length h max and percentage h max, respectively), an intermediate point location can be calculated, which is used as the union between the two profile curves previously mentioned. Once that point is determined, both curves are constructed, considering the values of the angles and length parameters which indicate the control point location of each curve, here indicated as first elevation angle and first drop angle for the case of the first curve, and second elevation angle and second drop angle for the case of the latter.

Figure 6C:
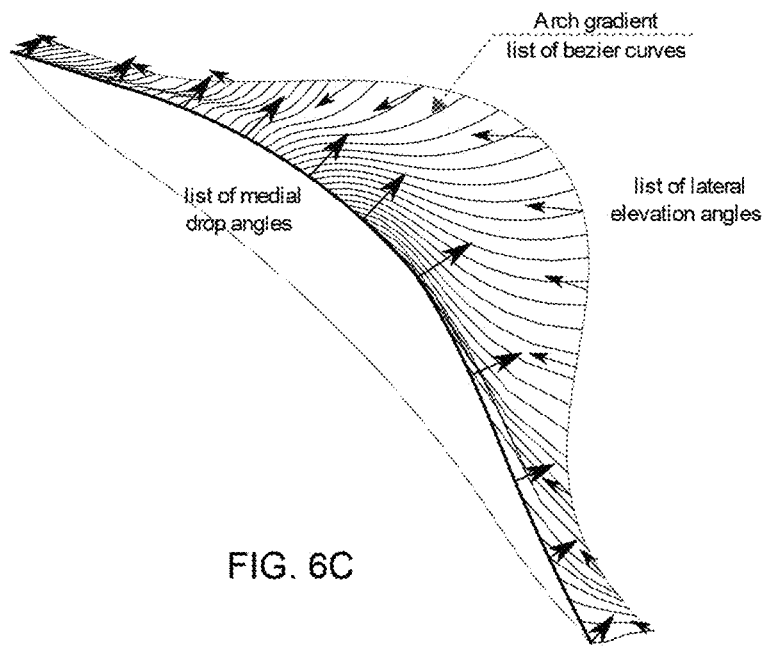

In a third step, the recently generated Arch profile is connected with the Arch inner edge, through a large number of additional curves, which in conjunction are called Arch gradient, shown in FIG. 6C. Each one of these curves is built considering the values of the angles and length parameters, here indicated as medial drop angle and lateral elevation angle, which define the control points needed. Those parameters are given in a list of values, each one of them for each curve.

Figure 6D:
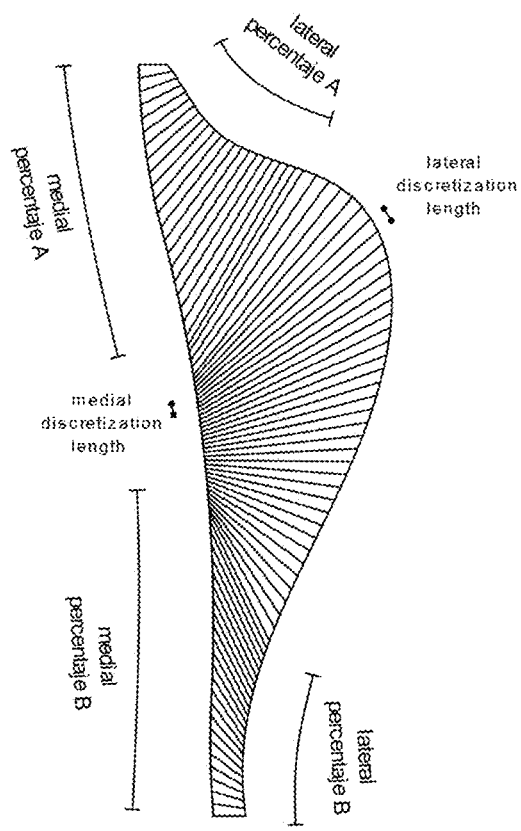

In a fourth step, an optimization in the distribution of the Arch gradient curves is carried out, shown in FIG. 6D, which takes into account another set of parameters, which define the discretization, or maximum separation between each pair of curves, here indicated as medial discretization length and lateral discretization length. Further, a new set of parameters are considered, to indicate which percentage sections of the outer edge are connected with the corresponding percentage sections of the inner edge, for controlling the overlapping between them.

Figure 6E:
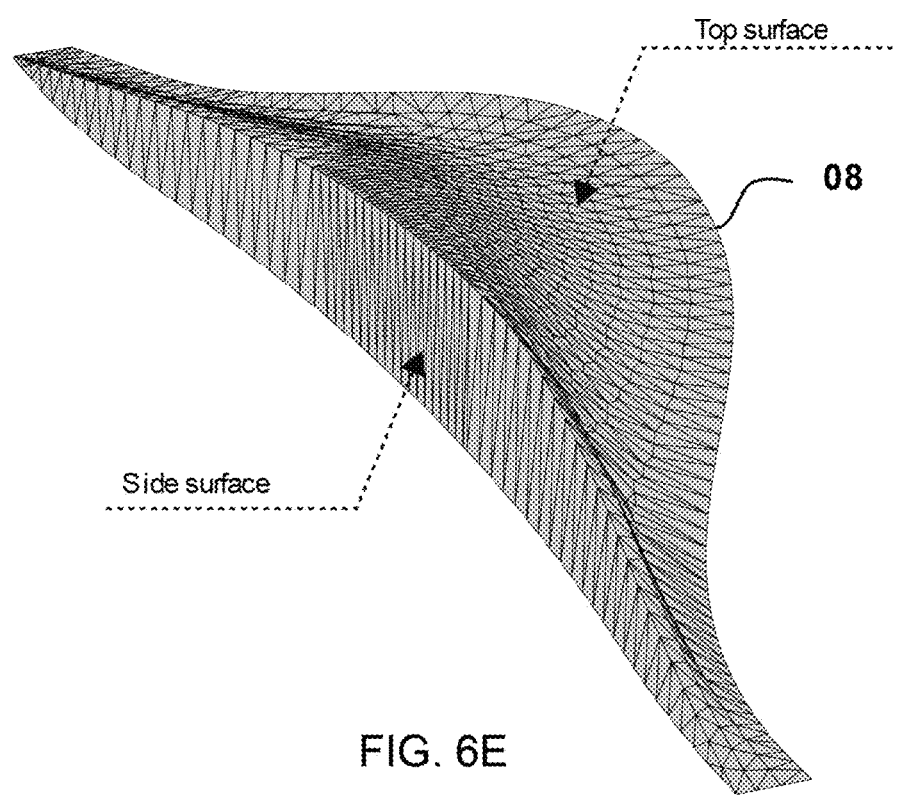

In a last step, based on the previously built Arch outer and inner edges, Arch profile, and Arch gradient, the construction of a Top surface and Side surface is carried out, as shown in FIG. 6E, through mesh discretization techniques, such as, for instance, Delaunay triangulation. The large number of faces connected by vertices then provide for the completion of the Longitudinal Arch.

Figure 7:
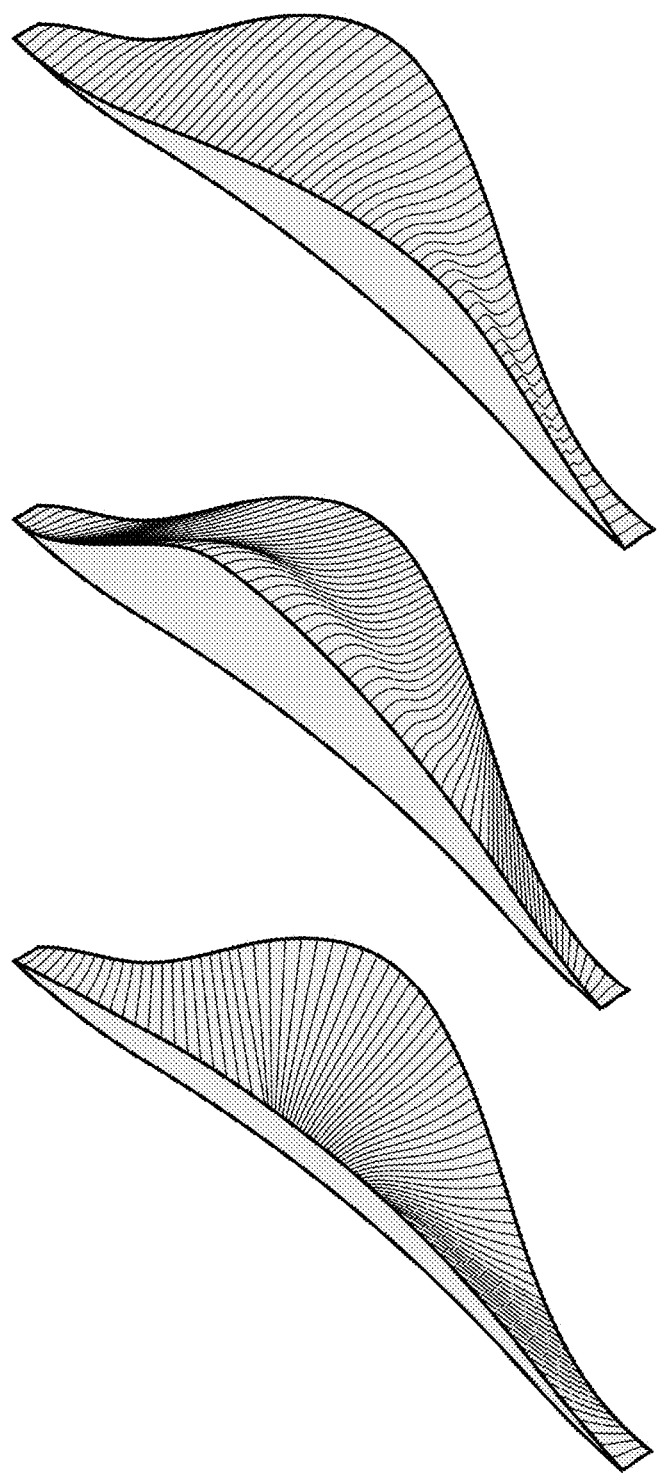
FIG. 7 illustrates the effect of the variation in the values of the given parameters, by creating different versions in the geometry of an element.

The variation in the values of the given parameters can create very different versions of a Longitudinal Arch, which allows to build an infinity of shapes for just one type of Insole Element 08. This feature provides the versatility required by the proposed method, to achieve the main goal, which is to obtain the best solution that fits an individual's needs. To illustrate this concept, it is show in the FIG. 7 a group of three Longitudinal Arches, built with the same Shapes 16 curves, but using different values for each set of parameters. It can be noticed the differences between them. Once again, the chosen values for the parameters would depends on the objective that is being pursued for this specific individual, which is defined based in the Implementation Instruments 12.

In summary, each insole Element 08 considered in the design method, which will be enumerated in the next section, is built following the same procedure described previously. That is, each insole Element 08 is constructed starting from a specific subset, chosen from the total number of calculated Shapes 16, and considers different Parameters 17 to create three dimensional surfaces made of faces and vertices. These geometries have to be versatile, robust and accurate.

ELEMENTS 08. The therapeutic insole 11 is made of a set of Insole Elements 08, which are located in specific zones along the foot, with a plurality of objectives. The inclusion of one or more Insole Elements 08 in the therapeutic insole design can respond to anomalies of the individual observed in the foot, or are established to reach improvements in the biomechanics performance of the lower limb, which is determined by the practitioner, or can obey to the activity that will be used for, or a plurality of other variables, as desired.

Figure 8:
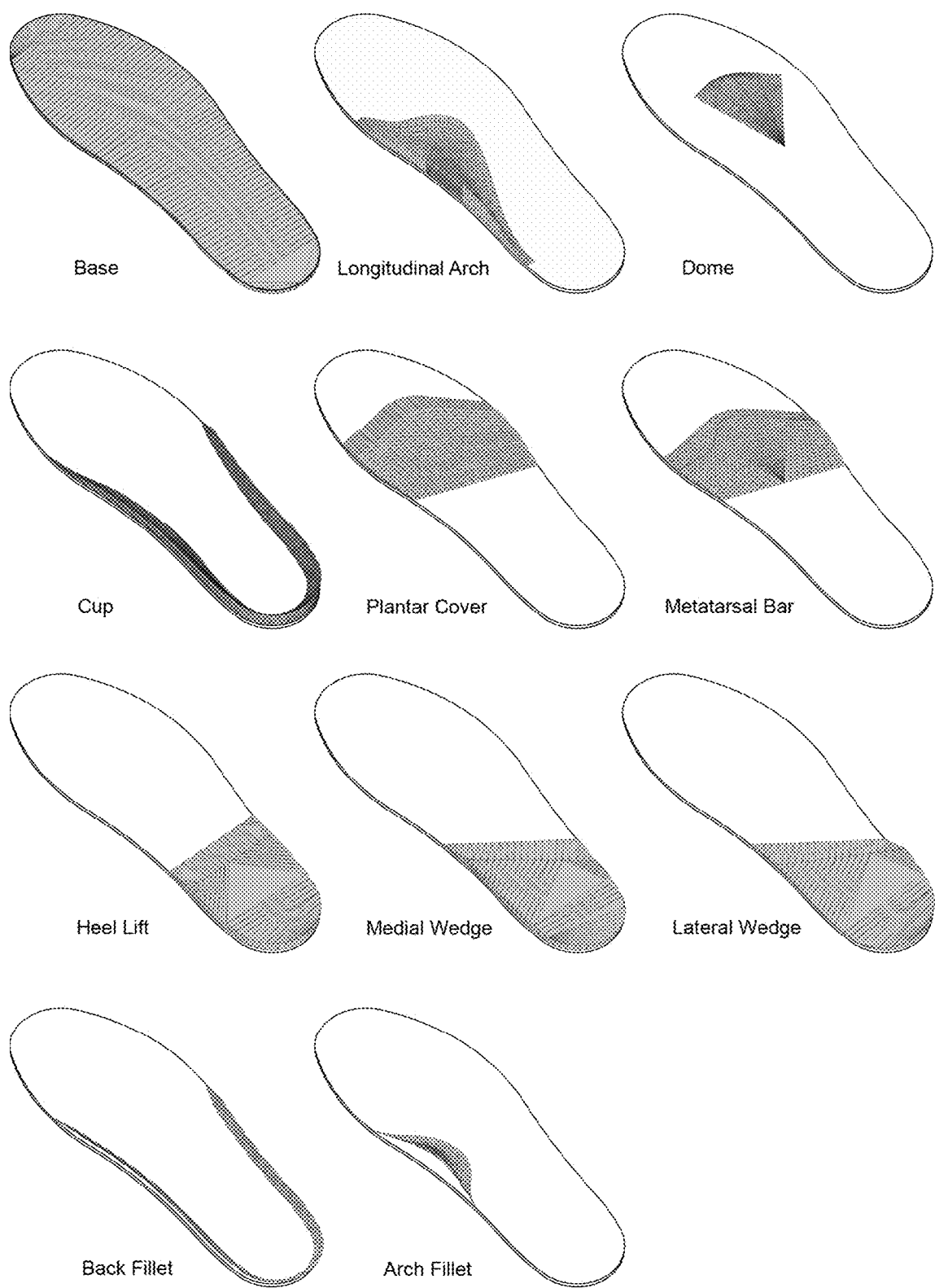
FIG. 8 shows a set of elements that can be considered in the therapeutic insole design method.

As shown in FIG. 8, a therapeutic insole can consider two or more Insole elements, from a large list of insole Elements 08 types. There is for example a Base, a Longitudinal Arch, a Dome, a Retrocapital Bar, a Plantar Cover, a Lateral Wedge, a Medial Wedge, a Heel Lift, a Fillet Back, a Fillet Arch, among others. The existence of the Insole Elements 08 included in a specific design, as well as their dependency and correlation between each other, are defined in the Systematic Review input 01, and are implemented in the method through the Implementation Instruments 12. This information can be complemented with a Finite Element Analysis 23 and/or Machine Learning 22 input, as it will be described in the embodiment 101.

3D MODEL 09. The set of Insole Elements 08 defined previously are created and correctly located, considering the Inner shape data 03, by the Algorithm-driven design 07. The whole group of created Insole Elements 08 together conform the 3D Model 09, which may be exported in an appropriated exchange format for later manufacturing (for instance, as stereolithography (STL) format).

In conjunction with the 3D Model 09, the process is finalized, by choosing the materiality and confection details needed for the specific individual, which is directly related with the activity that the insole will be used for.

MANUFACTURING 10. The manufacturing process of the insole is in charge of a manufacturer, that may be the same practitioner who carried out the design method process, or any other different entity. For that purpose, the technical specifications of the insole are delivered to the manufacturer, which consists in the materiality, the confection details of the insole and the data included in the 3D Model 09.

The therapeutic insole may be fabricated using an automated manufacturing machine, such as a computer numerical control (CNC) device. For instance, a X-Carve 750 mm by Inventables Inc. (United States) may be used, with Ethylene Vinyl Acetate foams provided by Ultralon (New Zealand) with a hardness ranging 30-200 JIS C degrees.

It may also be built with a 3D Printer device, which has to be able to use materials with appropriate mechanic behavior, such as Elastomeric Polyurethane by Carbon Inc. (United States), among others.

Figure 9:
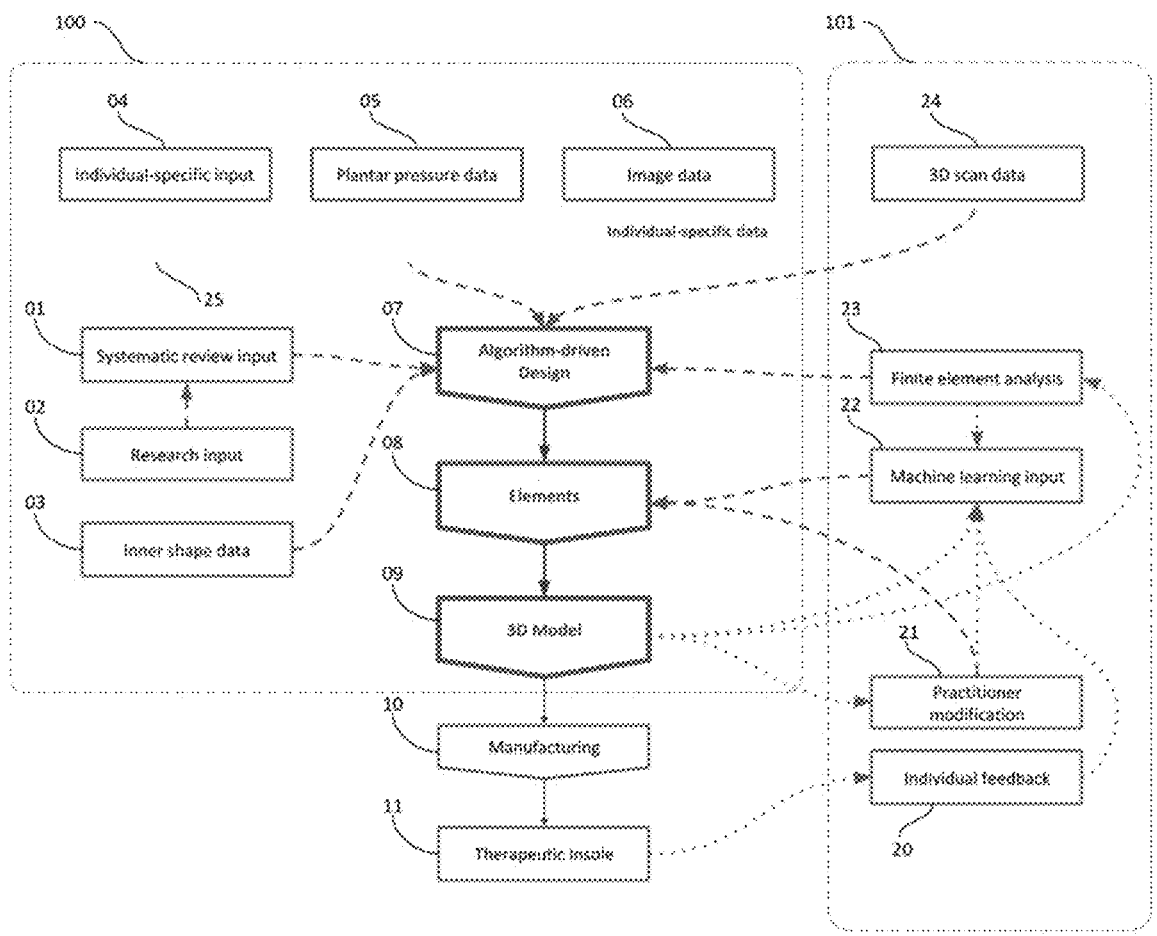
FIG. 9 is a flowchart showing an embodiment for a method, which incorporates a plurality of alternatives, such as: individual feedback, practitioner modification, machine learning systems and finite element analysis to a therapeutic insole design method.

COMPLEMENTARY PROCESSES 101. As shown in FIG. 9, the previously proposed method may be complemented with a set of additional processes, which can be list as follows:

Practitioner modification 21;
Individual feedback 20;
Finite element analysis 23;
Machine learning 22;
3D scan data 24.

Each one of these additional processes may be optionally implemented individually or together, depending on the insole needs, the practitioner requirements, or the individual requirements.

Practitioner modification 21. The group el Elements 08 defined, as well as the values of the Parameters 17 proposed automatically by the Algorithm-driven design 07 may be modified by a Practitioner, in case of it being required, to incorporate arbitrary criteria or new medical criteria not included in the Systematic Review 01 yet.

For example, a Practitioner could modify any of the Parameters 16 used to build the Longitudinal Arch, indicated previously in FIG. 6. These may be the length h max, percentage h max, elevation and drop angles 1, elevation and drop angles 2, list of medial drop angles, list of lateral elevation angles, medial percentages A and B, lateral percentages A and B, medial and lateral discretization lengths.

Individual feedback 20. Once the therapeutic insole 11 is delivered to the individual, a series of interviews are carried out, where the comfort feeling and insole effectiveness are registered, which conforms an Individual feedback 20. Those interviews are conducted a number of weeks after the insole has being used. As an example, an interview may be conducted at the end of the first, the fourth, and the twelfth week.

This Individual feedback allows to quantify all those variables which have a strong subjective component and depend on each individual. This interview is made following standard methodologies, such as those shown in questionnaires of the Foot & Ankle Disability Index (FADI) Score or the like, of international standard, which measure topics like pain, comfort and serviceability.

Finite element analysis 23. Considers analysis with finite element method 23 (FEA), for the material and geometry analysis of the insole and their mechanic behavior, when subjected to static and dynamic individual specific loads during their useful life.

Construction of a discrete mesh from the generated 3D Model 09, which chosen element size and type is made in accordance to the Systematic Review 01, implemented through the Implementation Instruments 12. An efficient approach, to solve the differential equations, that rule the finite element method, may be reached by choosing a proper relation between the size and the type of element. For example, in a linear analysis, and using linear type elements, the maximum size recommended for the discrete element has to be a fraction of the wavelength of the dynamic load. The element size may be decrease if the element type order increases, for example to quadrature type.

The mechanical properties of the materials that conform the insole are incorporated to the finite element model, based on the technical specifications of the materials available, indicated by the material supplier. Between those properties, there are stiffness related values like elasticity module, strength related like yield limit and rupture limit, damping related values like damping ratio, and mass related like density, among others.

The static and dynamic loads are incorporated to the finite element model, inferred from the Plantar pressure data 05, to represent the specific characteristics in the of the individual's gait and posture. These loads may be of concentrated and/or distributed type.

The results obtained with the Finite element analysis 23 may modify the values of the Parameters 17 originally calculated and the specified material, following the established objectives like redistribution of loads, energy dissipation and posture alignment.

Machine learning 22. A Machine learning system can be incorporated to the design method, which is able to learn from the individual design process of each individual, fed with the data and parameters used in the construction of the 3D Model 09, from the Practitioner modification 21 and the Individual feedback 20. The learning process carried out is considered to influence in the chosen of Parameters values in the design of future insoles, as Machine learning input 22.

The 3D Model 09 obtained is used to feed the Machine Learning system, following the objective of finding those dependency relations than may exist between the Elements 08 and the used Parameters 17. Those, which have no scientific evidence of correlation, may be detected and determined by the Learning system.

The obtained Individual feedback 20 is used to feed the Machine Learning system with the behavior of the individual, following the objective of finding those correlations than may exist between the manufactured Therapeutic Insole 11 and the comfort and effectiveness variable quantified in the feedback, which have high levels of subjectivity.

The Practitioner modification 21 obtained is used to feed the Machine learning system, following the objective of finding those cases in which the values calculated automatically by the Algorithm-driven design 07 are not good enough and make necessary an external modification.

The Finite element analysis 23 results are used to feed the Machine learning system, following the objective of finding those correlations that may exist between the fabricated Therapeutic insole 11 and the mechanical behavior of the insole subjected to the individual loads.

3D scan data 24. Includes a three-dimensional scanner, to register the foot shape during the acquisition of Individual-specific data. The additional information measured by this device may be relevant in some particular cases from exceptional individuals, which may present atypical conditions, like, for example, absence of fingers, malformations, and pathologies that may not be considered in the proposed design method indicated in FIG. 1.

The acquisition of 3D Scan data 24 may be made with a set of digital images obtained with a device to for that purpose, like a Nikon D90 photographic camera, put together to create a three-dimensional geometry with a reality capture software like ReCap Photo by Autodesk, among multiple other alternatives. The 3D Scan may be exported in an appropriated exchange format, for their implementation in the algorithm driven design 07 (for instance, as stereolithography (STL) format).

It will be appreciated by those skilled in the art that changes could be made to the embodiments described above without departing from the broad inventive concept thereof. It is understood, therefore, that this invention is not limited to the particular embodiments disclosed, but it is intended to at least cover all modifications within the spirit and scope of the present invention as described and depicted herein. Other embodiments will be apparent to those skilled in the art from consideration of the specification and practice of the disclosed method. For this reason, every modification in this sense, or similar is within the scope of the present invention.

The invention claimed is:

1. A method for the design of therapeutic insoles comprising:

providing a plurality of medical criteria about biomechanics of a lower extremity of a body and a plurality of therapeutic insole design criteria, which parameters are previously determined in an arbitrary manner;

providing a database with shape data information, which includes a shape and characteristics of shoe trademarks and models;

determining an individual-specific input by an exam and/or clinical interview based on the existence of concomitant pathologies and conditions, indicators of physical activities, posture observation, anatomical dimensions and foot anthropometry using a first device to measure a dynamic and/or static plantar pressure of the foot;

determining, by the first device, a set of plantar pressure data, for the measurement of foot function and gait analysis, during a determined interval of time;

using a second device to measure the alignment of bone segments of the lower extremity of the body;

determining, by the second device, a set of image data for the measurement of bone segments alignment of the lower extremity of the body and the relation between them;

wherein further including the following steps:

providing an algorithm-driven design to carry out the design of a plurality of three-dimensional elements, by determining at least the following:

a) a set of implementation instruments, which contains the mathematical and programming implementation of all the recommendations and medical criteria that were compiled in the systematic review and internal studies;

b) an individual characterization, which contain the diseases, pathologies, physical activities, and all the medical-related analysis, based on the individual-specific input obtained previously;

c) a set of plantar characterizations of the individual, which contain a footprint analysis and gait analysis, based on the data obtained by the first device;

d) a set of alignment characterizations of the individual bone-alignment, which contain a representation and inclination analysis, based on the data obtained by the second device;

e) a set of shapes are determined from the inner shape data and the plurality of characterizations, which are weighted individually or correlated;

f) a diversity of geometric parameters from the previously mentioned shapes, which value types include angles, lengths and percentages;

using said algorithm-driven design to determine the plurality of three-dimensional elements;

wherein the location and geometry of each three-dimensional element are calculated based on the mentioned shapes and parameters, and the correlation between them, where each of the three-dimensional element pursues one or more specific objectives, for the redistribution of anomalous pressure and/or alignment of bone segments;

conforming a 3D model based on the combination of at least two of the plurality of three-dimensional elements;

wherein the footprint analysis infers the geometry of a number of zones and quantities along the foot, based on the peak and mean pressure values, as measured in a dynamic pressure examination, through contour levels;

wherein the gait analysis is measured through at least three dynamic samples of each foot, and the standing of the individual; and wherein the set of obtained results with the footprint analysis and gait analysis, of all the plantar pressure data of the individual, are then individually weighted for the construction of the shapes.

2. A method according to claim 1, wherein the step of providing a plurality of medical criteria is done based on systematic reviews of published scientific articles with quantitative-theoretical ground.

3. A method according to claim 2, wherein the step of providing a plurality of medical criteria is also or exclusively done based on arbitrary input of third parties.

4. A method according to claim 1 wherein the step of providing a plurality of medical criteria is also or exclusively done based on arbitrary input of third parties.

5. A method according to claim 1, wherein:
prior to performing the algorithm-driven design, using a third device to measure a three-dimensional plantar shape, and determining by the third device, a 3D scan data;
wherein the step of providing an algorithm-driven design also includes:
using the 3D scan data to detect atypical conditions;
modifying the parameters according to the same.

6. A method according to claim 1, further including the following steps:

performing a finite element analysis on the 3D model, to provide for the redistribution of loads, energy dissipation and posture alignment;
wherein the step of providing an algorithm-driven design also includes:
using the data from said finite element analysis to modify the parameters.

7. A method according to claim 1, further including the following steps:
modifying the 3D model by a practitioner.

8. A method according to claim 1, further including the following steps:
providing individual feedback about the insole.

9. A method according to claim 1, wherein:
prior to performing the determination of insole elements, providing a computing device able to perform a machine learning process;
wherein said machine learning process is fed by any or all the following input:
said finite element analysis;
said 3D model;
said individual feedback;
said practitioner modification;
wherein said machine learning process modifies the insole elements.

10. A method according to claim 1, further including the following steps:
translating said 3D Model into an appropriated computer file using a standard 3D exchange format.

11. A method according to claim 10, wherein:
in the step of translating said 3D Model, said exchange format is STL.

12. A method according to claim 11, further including the step of:
manufacturing a therapeutic insole in an automated manufacturing machine using said computer file.

13. A method according to claim 10, further including the following steps:
manufacturing a therapeutic insole in an automated manufacturing machine using said computer file.

* * * * *